(12) United States Patent
Hellwig

(10) Patent No.: US 8,945,085 B2
(45) Date of Patent: Feb. 3, 2015

(54) METHOD AND DEVICE FOR CALCULATING A BOLUS AMOUNT

(75) Inventor: Robert Hellwig, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 1849 days.

(21) Appl. No.: 11/470,841

(22) Filed: Sep. 7, 2006

(65) Prior Publication Data
US 2007/0282299 A1    Dec. 6, 2007

Related U.S. Application Data

(63) Continuation of application No. PCT/EP2004/014733, filed on Dec. 27, 2004.

(30) Foreign Application Priority Data

Mar. 8, 2004   (DE) .......................... 10 2004 011 135

(51) Int. Cl.
*A61M 31/00*    (2006.01)
*A61M 5/172*    (2006.01)
*G06F 19/00*    (2011.01)
*A61M 5/142*    (2006.01)

(52) U.S. Cl.
CPC ......... *A61M 5/1723* (2013.01); *G06F 19/3468* (2013.01); *A61M 2005/14208* (2013.01); *A61M 2230/201* (2013.01)
USPC ......................................................... 604/504

(58) Field of Classification Search
CPC .......................... A61M 5/1723; G06F 19/3468
USPC ..................... 604/500–505, 65–67, 131, 151; 128/DIG. 12, DIG. 13
See application file for complete search history.

(56) References Cited

U.S. PATENT DOCUMENTS

| | | | |
|---|---|---|---|
| 5,822,715 A * | 10/1998 | Worthington et al. ........... 702/19 |
| 6,554,798 B1 * | 4/2003 | Mann et al. .................... 604/131 |
| 2003/0055570 A1 | 3/2003 | Ribero, Jr. |
| 2003/0060753 A1 * | 3/2003 | Starkweather et al. ......... 604/66 |
| 2003/0104982 A1 | 6/2003 | Wittmann et al. |

FOREIGN PATENT DOCUMENTS

| | | |
|---|---|---|
| DE | 3545260 A1 | 6/1987 |
| DE | 10057215 A1 | 5/2001 |
| EP | 1102194 * | 5/2001 |
| EP | 1 281 351 A2 | 2/2003 |

* cited by examiner

*Primary Examiner* — Manuel Mendez
(74) *Attorney, Agent, or Firm* — Dinsmore & Shohl LLP

(57) ABSTRACT

A method for calculating a bolus amount, wherein the bolus amount is calculated according to a basal rate, and a device for calculating a bolus amount according to the method, the device including an input unit used to input an amount of received carbohydrates, a computer coupled to the input unit and at least one interface used to transmit an actual blood glucose value and the value of the actual basal rate to the computer, wherein the at least one interface or another interface transmits a bolus amount calculated by the computer.

22 Claims, 1 Drawing Sheet

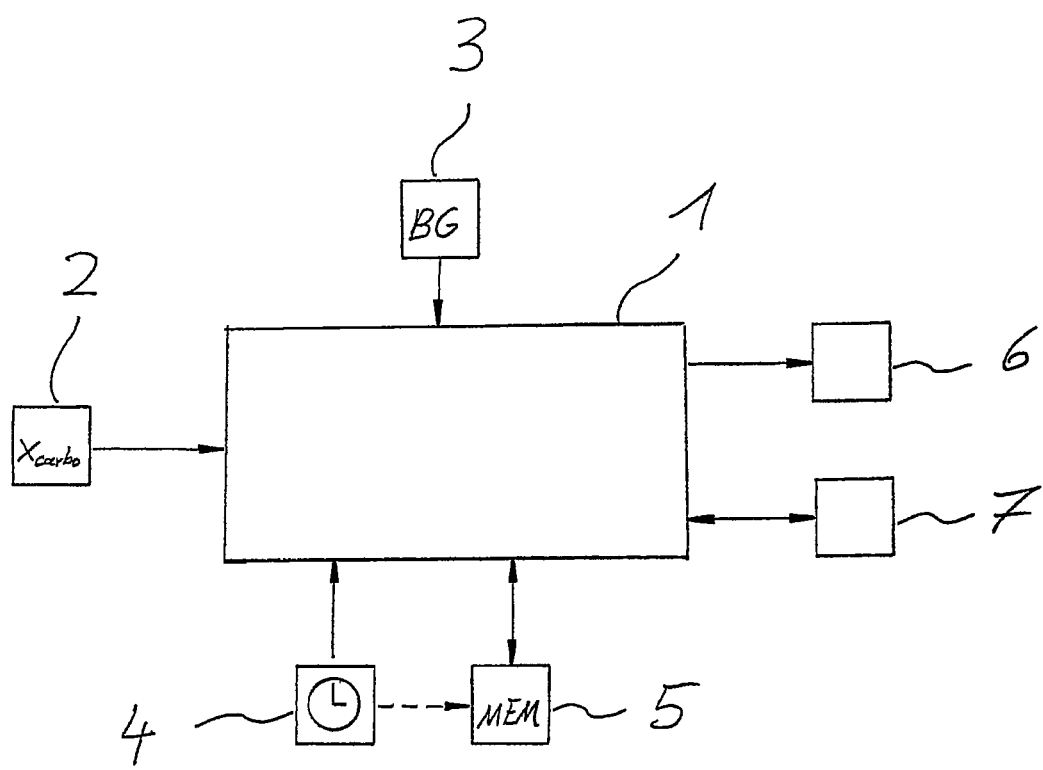

METHOD AND DEVICE FOR CALCULATING A BOLUS AMOUNT

CROSS-REFERENCE TO RELATED APPLICATION(S)

This application is a continuation of International Application No. PCT/EP2004/014733, filed on Dec. 27, 2004, which claims priority to German Application No. 10 2004 011 135.9, filed on Mar. 8, 2004, the contents of both of which are incorporated herein in their entirety by reference.

BACKGROUND

The present invention relates to devices for delivering, dispensing or administering substances, and to methods of making and using such devices. It also relates to methods for delivering, dispensing or administering substances, and to establishing, implementing and using such methods. More particularly, it relates to a method and a device for calculating a bolus amount, including for continuous subcutaneous administration of insulin by means of an insulin pump, whereby rapid-acting insulin can be administered to, for example, provide a patient with a bolus amount of insulin for the consumption of carbohydrates.

Human beings should have a blood glucose level of approximately between 70 and 126 mg/dl; with the help of insulin, glucose in the blood can be used as fuel in the body's cells to provide the body with vital energy. Normally, the insulin required is generated by the pancreas, which produces the requisite amount of insulin and releases it into the body. Diabetics need to be supplied with insulin artificially. Insulin pumps that are intended to completely or at least partially replace the function of the malfunctioning pancreas are often used for this purpose. Small quantities of insulin are continuously infused into a patient's subcutaneous fatty tissue over the course of the day, usually in the abdominal region, by means of a catheter; a quantity of insulin which is delivered continuously to a patient over the course of the day and which depends on the time of day may be referred to as the basal rate. (Note that, as used herein, the term "basal rate" is intended to mean a rate of supply, including continuous supply, of a chemical, substance or process for producing a desired effect, including, for example, a rate of insulin supply for controlling cellular glucose and amino acid uptake.) The basal insulin requirement differs from patient to patient and is subject to circadian fluctuations, so an insulin pump is programmed with the basal-rate profile in a patient-specific manner. When food is consumed, a larger amount of insulin, a so-called bolus, is needed to enable the body's cells to make use of the quantity of carbohydrate or sugar consumed in the food.

Thus, whenever patients want to consume carbohydrates or correct an elevated blood-glucose level, they are obliged to administer bolus insulin. The bolus amount required for this should be calculated as accurately as possible. A possible way of calculating a recommendation for the amount of insulin to be delivered is to use the following formula, which may be referred to as formula 1:

$$Rec[I.U.] = x_{carbohydrates}[g] * A_{meal}[I.U. * g^{-1}] +$$
$$(x_{BGactual}[mmol * l^{-1}] - B_{BGtarget}[mmol * l^{-1}] -$$
$$C_{insulin\ still\ effective}[I.U.] *$$
$$D_{correction}[mmol * l^{-1} * I.U.^{-1}]) *$$
$$(D_{correction}[mmol * l^{-1} * I.U.^{-1}])^{-1}.$$

In formula 1, the variable Rec [I.U.] refers to the recommended number of insulin units I.U. to be administered as a bolus, as calculated from the formula. To calculate the recommended number of insulin units to be delivered, two variable parameters are used, namely the parameter $x_{carbohydrates}$, which represents the amount, in grams, of carbohydrate consumed, or to be consumed, as food and the parameter $x_{BG\ actual}$, which represents the measured or actual blood-glucose value in mmol/l. The following, preset parameters are also used: $A_{meal}$, which represents the amount of insulin units needed to process or compensate for one gram of carbohydrate, $B_{BG\ target}$, which represents the target or nominal blood-glucose value in mmol/l, and $D_{correction}$, which indicates how the blood-glucose value is reduced by the effect of one unit of insulin in mmol/l per unit of insulin. The parameter $C_{insulin\ still\ effective}$ is used to take account of insulin that has already been injected or infused, it being possible to calculate this parameter on the basis of algorithms that can calculate the remaining activity of infused insulin in the body at a given time after infusion. The amount of insulin administered over a preceding period of e.g. 6 to 12 hours can be taken into account, for example.

If formula 1, as shown above, is used to calculate a bolus dose, constant values are preset for the parameters $A_{meal}$ and $D_{correction}$ over preset periods, depending on the time of day. For example, a value of 0.9 insulin units (I.U.) per bread unit (corresponding to 12 g of carbohydrate) is set for the parameter $A_{meal}$ for the period between 22:00 h and 06:00 h. A value of 1.5 insulin units per bread unit is set for the period between 6:00 h in the morning and 10:00 h in the morning, a value of 1.0 insulin units per bread unit between 10:00 h and 16:00 h, and a value of 1.4 insulin units per bread unit between 16:00 h and 22:00 h. The parameter $D_{correction}$ is assigned a constant value depending on the time of day in the same way, and, on the basis of these constants assigned to the parameters $A_{meal}$ and $D_{correction}$, a recommended number of insulin units to be administered as a bolus is calculated using formula 1.

A method for calculating a bolus value on the basis of a varying daily prediction of the amount of insulin required is known from U.S. Pat. No. 6,691,043 B2.

SUMMARY

In one embodiment, the present invention comprises a method and a device for calculating an amount of a substance to be administered, and for continuous administration of the substance by a pump or the like, whereby the substance to be administered can be administered to treat or affect a sensed amount or effect of another substance.

An object of the present invention is to provide a method and a device whereby a bolus recommendation can be established simply and reliably.

In one embodiment, the present invention comprises a method for calculating a bolus amount as a function of a basal rate.

In one embodiment, the present invention comprises a device for calculating a bolus amount, the device comprising an input unit for inputting an amount of carbohydrate consumed, a calculating or processing unit connected to the input unit, and at least one interface by which a current blood-glucose value and a current basal-rate value can be transmitted to the calculating or processing unit, said at least one interface also for transmitting a bolus amount ascertained by the calculating or processing unit.

In one embodiment, the present invention comprises a method for calculating a bolus amount (Rec), wherein the bolus amount (Rec) is calculated according to the basal rate (BR actual), and a device for calculating a bolus amount according to the method, the device comprising an input unit used to input an amount of received carbohydrates (x carbohydrates), a computer coupled to the input unit and at least one interface used to transmit an actual blood glucose value (x BG actual) and the value of the actual basal rate (BR actual) to the computer, wherein the at least one interface or another interface transmits a bolus amount (Rec) calculated by the computer.

BRIEF DESCRIPTION OF THE DRAWING

FIG. 1 shows an embodiment of a device according to the present invention for calculating a bolus amount.

DETAILED DESCRIPTION

In one embodiment of the method according to the present invention, the basal rate is used to calculate a bolus amount or a recommended number of insulin units to be administered to compensate for a quantity of carbohydrate consumed by a user. The bolus amount is calculated as a function of the actual basal rate, as a function of the basal rate, as a function of a basal-rate profile, or as a function of another suitable parameter. In some embodiments, the method according to the present invention is based on the fact that the basal rate, which is constantly changing over the course of the day, is correlated with the factors $A_{meal}$ and $D_{correction}$ described above. Thus, in some embodiments of the method according to the present invention, a bolus amount or a recommendation regarding the administration of an insulin dose as a bolus is calculated without using parameters that change abruptly according to preset periods; rather, a bolus amount that is as far as possible optimally tailored to a patient's individual situation in accordance with the circadian rhythm is calculated at each time during the course of the day.

In some preferred embodiments, the parameter $A_{meal}$ contained in formula 1 above is calculated using the following formula, which may be referred to as formula 2:

$$A'_{meal}[I.U.*g^{-1}] = CF_A[h*g^{-1}]*BR_{actual}[I.U.*h^{-1}]$$

In some preferred embodiments, the factor $D_{correction}$ contained in formula 1 may be calculated using the following formula, which may be referred to as formula 3:

$$D'_{correction}[mmol*l^{-1}*I.U.^{-1}] = CF_D[mmol*l^{-1}*h*I.U.^{-2}]*BR_{actual}[I.U.*h^{-1}]$$

Using formulae 2 and 3 above, the parameters $A'_{meal}$ and $D'_{correction}$ can be calculated as a function of the current basal rate, the current basal rate $BR_{actual}$ being multiplied by the constant factors $CF_A$ and $CF_D$ respectively. The factor $CF_A$ is a constant which describes the correlation between the parameter $A_{meal}$ and the current basal rate $BR_{actual}$, which gives the current basal rate in insulin units per hour, for example. Correspondingly, the factor $CF_D$ is a constant which describes the correlation between the parameter $D_{correction}$ and the current basal rate $BR_{actual}$.

The actual or current basal rate $BR_{actual}$ may be stored, e.g., in a memory of a PC, an organizer, a pump, or another suitable device or instrument, including portable devices or instruments, or it can be ascertained, e.g., from an amount of the daily insulin requirement. This can be done, for example, using the known method of Renner et al., as described, for example, in Disetronic's "Informationen zur Insulinpumpen—Therapie (CSII) [Information on Insulin Pump Therapy (CSII)]" booklet (incorporated herein by reference), whose content is based on the insulin pump seminars of the Diabetes Center at the clinical complex in Bogenhausen, Munich. Reference may also be made to the article "PROSPEKTIVE EVALUATION EINER STANDARDISIERTEN BASALRATENVERTEILUNG DIE CSII BEI TYP-I-DIABETES ÜBER 6 MONATE" [PROSPECTIVE EVALUATION OF STANDARDIZED BASAL-RATE DISTRIBUTION CSII IN TYPE I DIABETES OVER 6 MONTHS] by Wizemann, E., Renner, R., and Hepp, K. D. of Medical Department III and the Diabetes Center at the hospital in Bogenhausen, Munich, which was published as an abstract in DIABETES UND STOFFWECHSEL, ZEITSCHRIFT FÜR ANGEWANDTE DIABETOLOGIE [DIABETES AND METABOLISM, JOURNAL FOR APPLIED DIABETOLOGY], 36th Annual Conference of DEUTSCHE DIABETES-GESELLSCHAFT [GERMAN DIABETES SOCIETY] on May 23-26, 2001 in Aachen, Vol. 10, Supplement No. 1, May 2001 (both of which are incorporated herein by reference).

If the parameters $A_{meal}$ and $D_{correction}$ in formula 1 above are replaced by the parameters $A'_{meal}$ and $D'_{correction}$ defined or determined by formulae 2 and 3, the calculated recommended bolus amount Rec becomes a function of the current, constantly changing basal rate $BR_{actual}$ and thus does not show any abrupt changes of the kind seen when estimated values are used for $A_{meal}$ and $D_{correction}$, which are assigned constant values for preset times of day.

The factor $CF_A$ in formula 2 can be calculated if at least one value for $A_{meal}$ together with information regarding the time at which this parameter $A_{meal}$ applies is known. The factor $CF_A$ can be calculated generally from the following formula, which may be referred to as formula 4:

$$(CF_A)_i[h*g^{-1}] = n*\left(\sum_{k=1}^{n} BR_k[I.U.*h^{-1}]\right)^{-1} *(A_{meal})_i[I.U.*g^{-1}]$$

Here, k is $\geq 1$ and an index for the specific hours of the day at which $A_{meal}$ applies. $n \geq 1$ represents the number of hours at which $A_{meal}$ applies. $i \geq 1$ is an index for the individual factors $A_{meal}$ and $CF_A$. $(A_{meal})_i$ represents the factor $A_{meal}$ which applies during the hours k. $(CF_A)_i$ is a constant factor $CF_A$, which is obtained from $(A_{meal})_i$.

If only one factor $A_{meal}$ is used to determine $CF_A$, the following formula, which may be referred to as formula 5, may be used:

$$CF_{Ai\ [h*g^{-1}]} = (CF_A)_i[h*g^{-1}]$$

If more than only one factor $A_{meal}$ is used to determine $CF_A$, the following formula, which may be referred to as formula 6, may be used:

$$CF_A[h*g^{-1}] = n^{-1}\sum_{i=1}^{n}(CF_A)_i[h*g^{-1}]$$

Correspondingly, the factor $CF_D$ is calculated generally from the following formula, which may be referred to as formula 7:

$$(CF_D)_i [\text{mmol} * l^{-1} * h * I.U.^{-2}] = n * \left( \sum_{k=1}^{n} BR_k [I.U. * h^{-1}] \right)^{-1} * (D_{correction})_i [\text{mmol} * l^{-1} * I.U.^{-1}]$$

Here, k is ≥1 and an index for the specific hours of the day at which $D_{correction}$ applies. n≥1 represents the number of hours at which $D_{correction}$ applies. i≥1 is an index for the individual factors $D_{correction}$ and $CF_D$. $(D_{correction})_i$ represents the factor $D_{correction}$ which applies during the hours k. $(CF_D)_i$ is a constant factor $CF_D$, which is obtained from $(D_{correction})_i$.

If only one factor $D_{correction}$ is used to determine $CF_D$, the following formula, which may be referred to as formula 8, may be used:

$$CF_D [\text{mmol} * l^{-1} * h * I.U.^{-2}] = (CF_D)_i [\text{mmol} * l^{-1} * h * I.U.^{-1}]$$

If more than only one factor $D_{correction}$ is used to determine $CF_D$, the following formula, which may be referred to as formula 9, may be used:

$$(CF_D)[\text{mmol} * l^{-1} * h * I.U.^{-2}] = n^{-1} \sum_{i=1}^{n} (CF_D)_i [\text{mmol} * l^{-1} * h * I.U.^{-2}]$$

By directly incorporating the basal rate using the formulae described above, the method according to the present invention thus makes it possible to calculate a bolus amount which is better tailored to an individual patient and which does not show abrupt changes over time, as the bolus amount is ascertained on the basis of the constantly changing basal rate.

In some embodiments, the present invention also relates to and/or comprises a computer program which, when loaded on a computer or running on a computer, microprocessor or the like, executes the method of the present invention as described herein. The present invention also relates to and/or encompasses to a program storage medium or computer product with such a program.

In some embodiments, the present invention also relates to and/or comprises a device for determining or calculating an amount of insulin to be administered to a person as a bolus for the purposes of maintaining an appropriate blood-glucose level, with an input unit, such as, for example, a keypad, a touch screen or the like, for inputting an amount of carbohydrate $x_{carbohydrates}$ which a person is intending to consume and for inputting the current blood-glucose value $x_{BG\ actual}$, these parameters also being transmissible to the device via a suitable interface or interfaces, for example. In some embodiments, the device further comprises a calculating or processing unit, which calculates a recommendation Rec in respect of the bolus amount on the basis of the values input for $x_{carbohydrates}$ and $x_{BG\ actual}$, according to the method described herein. In some embodiments, the device further comprises an output unit by which the recommendation Rec established by the calculating unit is output and, for example, shown on a display and/or transmitted to an infusion pump via the interface, interfaces or other suitable feature or method, e.g., wirelessly.

In some embodiments, the device according to the present invention can have a known blood-glucose measuring device by which the current blood-glucose value $x_{BG\ actual}$ is measured and transmitted to the device, such that a user, to calculate a bolus amount required, only needs to input the amount of carbohydrate $x_{carbohydrates}$ that he or she proposes to consume.

In some preferred embodiments, the device according to the present invention has a memory, such as a RAM, for example, so that it is possible to store, for example, values for the basal rate BR, which changes over the course of the day, and/or to store how much insulin has already been administered and at what time. Other parameters, functions, data, operations, etc. may be stored and accessed as well.

In some embodiments, a timing unit, such as a clock or the like, is provided so that it is possible to ascertain an appropriate bolus amount depending on the time of day and to store an administered amount of insulin in a memory for further calculations with, for example, a time-stamp function.

FIG. 1 shows an embodiment of the device according to the present invention for calculating a bolus amount, with a calculating unit 1, connected to an input unit 2, such as a keypad for example, for inputting the amount of carbohydrate $x_{carbohydrates}$ which will be consumed or has been consumed by a user. The calculating unit 1 is also connected to a sensor 3 for measuring the current blood-glucose value. A time indicator, such as a clock 4 for example, provides information about the time of day to the calculating unit 1 and, optionally, to a memory 5, which can be read from and written to by the calculating unit 1, so that the amount of insulin (for example) administered can be stored, together with the time of administration, in the memory 5 and be read off for the new calculation of a bolus amount. The bolus amount ascertained by the calculating unit 1 can be output to a display, such as a screen or LCD display 6, for example. The bolus amount ascertained by the calculating unit 1 can be output directly to an insulin pump 7 which may then immediately effect delivery of rapid-acting insulin in accordance with the bolus amount ascertained.

In some embodiments, the time course of the basal rate may be stored in the pump 7, as in the memory 5, this time course being transmitted to the calculating unit 1 by the pump 7 and/or the memory 5 so that the bolus amount can be calculated according to the invention.

In some embodiments, the other above-described factors or parameters, or other functions, parameters, date, etc. for calculating the bolus amount or for other purposes, which have been input via the input unit 2 during configuration of the device according to the present invention, may be stored in the memory 5.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to a particular use contemplated. All such modifications and variations are within the scope of the invention as determined by the appended claims when interpreted in accordance with the breadth they are fairly, legally, and equitably entitled.

The invention claimed is:

1. A method for calculating a bolus amount for a patient on the basis of a constantly changing basal rate, a time course of the constantly changing basal rate being stored in a memory connected to a microprocessor, the method comprising:
- providing to the microprocessor an amount of carbohydrate to be consumed;
- providing to the microprocessor a blood glucose level measured on a blood glucose measuring device;
- providing to the microprocessor a nominal blood glucose value;
- providing to the microprocessor information about a current time of day;
- calculating with the microprocessor a value for an amount of insulin needed to process one gram of carbohydrate at the current time ($A'_{meal}$), said calculating being based on a factor correlating $A'_{meal}$ and a value of the constantly changing basal rate for the current time of day ($BR_{actual}$); and
- calculating with the microprocessor the bolus amount using the amount of carbohydrate to be consumed, the blood glucose level, the nominal blood glucose value, and $A'_{meal}$.

2. The method as claimed in claim 1, wherein $BR_{actual}$ is ascertained from a preset amount of a daily insulin requirement.

3. The method as claimed in claim 1, further comprising calculating with the microprocessor a value for reduction of a blood-glucose value by one unit of insulin at the current time ($D'_{correction}$) using $BR_{actual}$, and wherein calculating the bolus amount further comprises using $D'_{correction}$.

4. The method of claim 3 wherein $D'_{correction}$ is calculated using the following formula:

$$D'_{correction}[mmol*l^{-1}*I.U.^{-1}] = CF_D [mmol*l^{-1}*h*I.U.^{-2}]*BR_{actual}[I.U.*h^{-1}]$$

where $CF_D$ is a constant.

5. The method of claim 4 wherein $CF_D$ is calculated using the following formula:

$$n * \left(\sum_{k=1}^{n} BR_k [I \cdot U \cdot * h^{-1}]\right)^{-1} * (D_{correction})_i [mmol * l^{-1} * I \cdot U \cdot^{-1}]$$

where $D_{correction}$ represents a constant value of the reduction of blood-glucose by one unit of insulin over a preset period of hours depending on the time of day; k is ≥1 and is an index for the specific hours of the day at which $D_{correction}$ applies; n is ≥1 and represents the number of hours at which $D_{correction}$ applies; i is ≥1 and is an index for the individual factors $D_{correction}$ and $CF_D$; and $(D_{correction})_i$ represents the factor $D_{correction}$ during the hours k.

6. The method as claimed in claim 1, wherein at least one preset parameter is used to calculate the bolus amount.

7. The method as claimed in claim 6, wherein the nominal blood-glucose value is the preset parameter.

8. The method as claimed in claim 1, further comprising calculating with the microprocessor an amount of insulin that has already been infused, and wherein calculating the bolus amount further comprises using the amount of insulin that has already been infused.

9. The method of claim 1 wherein the factor which correlates $A'_{meal}$ and $BR_{actual}$ is calculated using the following formula:

$$CF_A[h*g^{-1}]*BR_{actual}[I.U.*h^{-1}]$$

where $CF_A$ is the factor which applies at the current time.

10. The method of claim 9, further comprising calculating with the microprocessor the factor $CF_A$ using the following formula:

$$n * \left(\sum_{k=1}^{n} BR_k [I \cdot U \cdot * h^{-1}]\right)^{-1} * (A_{meal})_i [I \cdot U \cdot * g^{-1}]$$

where $A_{meal}$ represents a constant value of the amount of insulin units needed to compensate for one gram of carbohydrates over a preset period of hours depending on the time of day; k is ≥1 and is an index for the specific hours of the day at which $A_{meal}$ applies; n is ≥1 and represents the number of hours at which $A_{meal}$ applies; i is ≥1 and is an index for the individual factors $A_{meal}$ and $CF_A$; and $(A_{meal})_i$ represents the factor $A_{meal}$ during the hours k.

11. The method of claim 1 wherein the amount of carbohydrate to be consumed is provided by inputting on an input device.

12. The method of claim 1 further comprising transmitting the bolus amount to an infusion pump, and administering the bolus amount.

13. The method of claim 12 wherein the bolus amount is transmitted to the infusion pump using an interface or a wireless transmitter and further comprising displaying the bolus amount on an output device.

14. The method of claim 1 further comprising storing the nominal blood glucose value in the memory.

15. A method for calculating a bolus amount on the basis of a constantly changing basal rate, a time course of the constantly changing basal rate being stored in a memory connected to a microprocessor, the method comprising
- providing to the microprocessor an amount of carbohydrate to be consumed;
- providing to the microprocessor a blood glucose level measured on a blood glucose measuring device;
- providing to the microprocessor a nominal blood glucose value;
- providing to the microprocessor information about a current time of day;
- calculating with a microprocessor a value for an amount of insulin needed to process one gram of carbohydrate at the current time ($A'_{meal}$), said calculating being based on a factor correlating $A'_{meal}$ and a value of the constantly changing basal rate for the current time of day ($BR_{actual}$);
- calculating with the microprocessor a value for the reduction of a blood-glucose value by one unit of insulin at the current time ($D'_{correction}$) using $BR_{actual}$; and
- calculating with the microprocessor the bolus amount using the amount of carbohydrate to be consumed, the blood glucose level, the nominal blood glucose value, $A'_{meal}$ and $D'_{correction}$.

16. The method as claimed in claim 15, further comprising ascertaining with the microprocessor $BR_{actual}$ from a preset amount of a daily insulin requirement.

17. The method as claimed in claim 15, further comprising calculating with the microprocessor the bolus amount using at least one preset parameter, wherein the nominal blood-glucose value is the preset parameter.

18. The method as claimed in claim 15, further comprising calculating with the microprocessor an amount of insulin that has already been infused, and wherein calculating the bolus amount further comprises the amount of insulin that has already been infused.

19. The method of claim 15 further comprising transmitting the bolus amount to an infusion pump, and administering the bolus amount.

20. The method of claim 15 further comprising storing the nominal blood glucose value in the memory.

21. The method of claim 15 wherein the factor which correlates $A'_{meal}$ and $BR_{actual}$ is calculated using the following formula:

$$CF_A[h*g^{-1}]*BR_{actual}[I.U.*h^{-1}]$$

where $CF_A$ is the factor which applies at the current time.

22. The method of claim 21 wherein $D'_{correction}$ is calculated using the following formula:

$$D'_{correction}[mmol*l^{-1}*I.U.^{-1}] = CF_D[mmol*l^{-1}*h*I.U.^{-2}]*BR_{actual}[I.U.*h^{-1}]$$

where $CF_D$ is a constant.

* * * * *